United States Patent [19]

Baum et al.

[11] 4,226,777
[45] Oct. 7, 1980

[54] 3-FLUORO-3-NITROOXETANE

[75] Inventors: Kurt Baum, Pasadena; Philip T. Berkowitz, Santa Ana, both of Calif.

[73] Assignee: The United States of America as represented by the Secretary of the Navy, Washington, D.C.

[21] Appl. No.: 59,920

[22] Filed: Jul. 20, 1979

Related U.S. Application Data

[63] Continuation-in-part of Ser. No. 933,364, Aug. 14, 1978, abandoned.

[51] Int. Cl.$^3$ .......................................... C07D 305/08
[52] U.S. Cl. .................................... 260/333; 528/70; 149/19.4
[58] Field of Search ........................................ 260/333

[56] References Cited

U.S. PATENT DOCUMENTS

| 2,995,571 | 8/1961 | Harris, Jr. ............................ 260/333 |
| 3,125,581 | 3/1964 | Coffman et al. ............. 260/544 F X |

OTHER PUBLICATIONS

Neilsen, et al., Tetrahedron, 22, (3), pp. 925–930, 1966.

Primary Examiner—Joseph Paul Brust
Attorney, Agent, or Firm—R. S. Sciascia; W. Thom Skeer; Lloyd E. K. Pohl

[57] ABSTRACT

3-Fluoro-3-nitrooxetane is prepared by a method which comprises reacting 2-fluoro-2-nitro propanediol with trifluoro methane sulfonic anhydride, separating the reaction product and then further reacting the reaction product with a base. The oxetane may be polymerized to form a nitro containing polyether which is useful as a binder material for explosives or propellants.

6 Claims, No Drawings

3-FLUORO-3-NITROOXETANE

CROSS-REFERENCES TO RELATED APPLICATIONS

This application is a continuation-in-part of U.S. patent application Ser. No. 933,364 which was filed Aug. 14, 1978 and is now abandoned.

BACKGROUND OF THE INVENTION

This invention relates to the preparation of 3-fluoro-3-nitrooxetane and the use of this compound as a precursor for nitro containing polyethers. Nitro containing polyethers have utility as explosives and propellant binders. The only known nitrooxetane that has been prepared prior to this invention is 3,3-bis(nitromethyl)oxetane, prepared by A. T. Neilsen and W. G. Finnegan. It is reported in Tetrahedron, 22, 925 (1966). This nitrooxetane was prepared in only 3% yield. Fluorooxetanes have been prepared by the reaction of olefins and fluoro ketones as described in U.S. Pat. No. 2,995,571 and U.S. Pat. No. 3,125,581. This method of preparation does not however lead to nitrated oxetane which would be suitable for explosives and propellants.

As mentioned previously the method for preparation of 3,3-bis(nitromethyl)oxetane has too low a yield to provide a satisfactory source for producing nitrooxetane in any quantity. There is thus a need for an efficient practical method of making nitrooxetanes in substantial yields and a high degree of purity.

SUMMARY OF THE INVENTION

The present invention comprises reacting 2-fluoro-2-nitropropanediol with trifluoromethane sulfonic (triflic) anhydride to give the monotriflate. The latter reacts with a base to give the desired oxetane.

DESCRIPTION OF THE PREFERRED EMBODIMENT

In accordance with this invention it has been discovered that when 2-fluoro-2-nitropropanediol reacts with trifluoromethane sulfonic anhydride a monotriflate is formed. Reaction of the monotriflate with a base yields 3-fluoro-3-nitrooxetane. The reactions involved may be illustrated by the following equations.

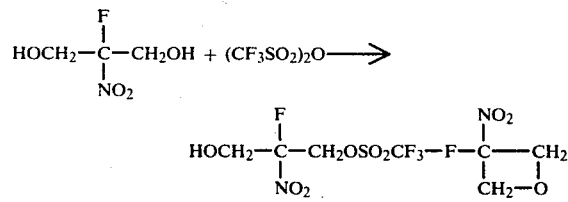

The reaction which results in the formulation of the monotriflate may be conducted in pyridine at a low temperature in the presence of ethyl ether. The monotriflate may then be separated by conventional chemical methods such as chromatography and solvent extraction and reacted with a base to form the oxetane. Both inorganic and organic bases have been found suitable for use in the formation of the oxetane. The nitrooxetane may then be isolated by conventional chemical methods such as chromatography and vacuum distillation.

The following examples illustrate the best mode known to the inventor for carrying out the process of this invention. It should be understood, however, that the conditions of the reactions described therein are by no means intended to limit the scope of this invention.

EXAMPLE I

A solution of 10.9 ml (0.65 mol) of triflic anhydride in 210 ml of ether was added dropwise over 25 minutes to a solution of 17.4 g (0.124 mol) of 2-fluoro-2-nitro-1,3-propanediol and 6.0 ml (0.074 mol) of pyridine in 210 ml of ether, at a temperature just below 26° C. After 16 hours, the resulting precipitate was filtered and washed with ether. The filtrate was stripped of solvent and the residue was partitioned between 300 ml of methylene chloride and 60 ml of water. The methylene chloride layer was washed with 30 ml of water, dried over sodium sulfate and chromatographed on a 125 g silica gel column. Elution with 500 ml of methylene chloride and with 1100 ml of 9:1 methylene chloride-ethyl acetate gave 15.5 g (88% yield) of 2-fluoro-2-nitro-1,3-propanediol monotriflate, which was recrystallized from methylene chloride. Skelly F: mp 29°–30°; proton NMR (CDCl$_3$) δ2.65 (broad s, 1H,OH), 4.10 (d,J=14 Hz, 2H, CH$_2$OH), 5.07 (m, J=14 Hz, 2 H CH$_2$O-SO$_2$CF$_3$); fluorine NMR (CDCl$_3$) φ72.0 (s, 3F, CF$_3$), 139.4 (quint, J=14 Hz, 1F, O$_2$NCF): IR (CH$_2$Cl$_2$) 3625 (OH), 1580, 1350 (NO$_2$), 1420, 1220, 1140, 900 (OSO$_2$CF$_2$), 1000 cm$^{-1}$ (CF).

Anal. Calcd for C$_4$H$_5$F$_4$NSO$_6$: C, 17.22; H, 186; N, 5.17. Found: C, 17.82; H, 1.75; N, 5.31.

Extracting the combined aqueous solutions with three 100 ml portions of ethyl acetate gave 8.7 g of recovered 2-fluoro-2-nitro-1,3-propanediol, which was dried by adding and stripping toluene.

EXAMPLE II

To a solution of 0.271 g (1.00 mmol) of 2-fluoro-2-nitro-1,3-propanediol monotriflate in 26 ml of water was added 1.00 ml of M KOH (1.00 mmol). Addition of KOH gave an orange solution. After stirring for 1 hour, the reaction mixture was extracted with methylene chloride (2×10 ml). The solution was dried over sodium sulfate and the methylene chloride was distilled off to leave an orange liquid residue. Preparative GLC (8 ft×0.375 in. column of 12% QF-1 on Chromosorb W, 100° C.) gave 0.017 g (14.0%) of 3-fluoro-3-nitrooxetane: $^1$HNMR (CDCl$_3$) δ4.97 (multiplet of 6); $^{19}$FNMR (CDCl$_3$) φ127.7 (multiplet of 5, J=14 Hz); IR (CH$_2$CH$_2$) 1575, 1345 (—NO$_2$), 1000 (C−F) cm$^{-1}$; n$_D^{24.5}$=1.4281.

Anal. Calcd for C$_3$H$_4$FNO$_3$ (120.067): C, 29.76; H, 3.33; N, 11.58. Found: C, 30.13; H, 3.35; N, 12.07.

EXAMPLE III

To a solution of 5.42 g (0.020 mol) of 2-fluoro-2-nitro-1,3-propanediol monotriflate in 36 ml of methylene chloride was added a solution of 3.1 ml (0.0207 mol) of 1,5-diazabicyclo-(5.4.0) undec-5-ene (DBU) in 18 ml methylene chloride dropwise over 12 minutes (below 24° C.). The reaction mixture was stirred for 75 minutes. Chromatography on a 30 g silica gel column and elution with methylene chloride gave 2 g of crude oxetane. Vacuum distillation gave 1.486 g (61.4%) of 3-fluoro-2-nitrooxetane: bp 31° (1.5 mm). The use of the silica gel column for removal of the DBU triflic acid salt was employed as the salt was not extracted from methylene chloride by water.

The process of this invention may be carried out continuously, semi-continuously or in a batch-wise fashion using commercially available equipment and materials. It will be appreciated by those skilled in the art that many obvious variations and modifications may be made in the process of this invention.

While two bases are specified above, i.e., KOH and 1,5-diazabicyclo-(5.4.0) undec-5-ene, other bases may be used in the formation of the oxetane. For example, other alkali metal hydroxides can be used in lieu of KOH.

Oxetanes are normally polymerized by means of a variety of Lewis acid catalysts. It was found, however, that the commonly used Lewis acid, boron trifluoride, did not polymerize 3-fluoro-3-nitrooxetane. Experimentation with other catalysts was then carried out. This experimentation resulted in the finding that polymerization could be accomplished in methylene chloride with the use of phosphorous pentafluoride as a catalyst. The resulting polymer was found to be soluble in dimethyl formamide and in dimethyl sulfoxide. The molecular weight, as determined by vapor osmometry in dimethyl formamide, was 2500. The polymer was shown by NMR to be a diol. It had a melting point of 234° C. and begain to decompose at 290°. Its density was 1.5885.

Since the polymer is a diol, it may be reacted with diisocyanates to give polyurethanes. The curing of diols with diisocyanates to form binders for explosives and propellants is well known.

EXAMPLE IV

Phosphoruous pentafluoride was bubbled with stirring into a solution of 0.122 g (0.001 mole) of 3-fluoro-3-nitrooxetane in 1.2 ml of methylene chloride. A white solid precipitated, and the addition of phosphorous pentafluoride was continued until no additional solid separated. Methanol (0.2 ml) was added, and the precipitate was filtered and was washed with methylene chloride to give 0.10 g of poly(3-fluoro-3-nitro-1,3-propylene) ether, with the properties described above.

To use a nitro containing polyether as an explosive, one may initiate a detonation by means of any common detonator known to the art.

What is claimed is:

1. A compound having the structure:

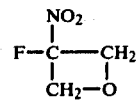

2. A process for the production of 3-fluoro-3-nitro oxetane comprised of the steps of; reacting 2-fluoro-2-nitro propanediol dissolved in pyridine with trifluoro methane sulfonic anhydride dissolved in ether at a temperature just below 26° C. for about 16 hours to form a monotriflate and reacting the monotriflate with a base.

3. A process according to claim 1 wherein the monotriflate is separated by means of chromatography prior to reacting it with a base.

4. A process according to claim 1 wherein the base is an alkali metal hydroxide.

5. A process according to claim 1 wherein the base is potassium hydroxide.

6. A process according to claim 1 wherein the base is 1,5 diazabicyclo (5.4.0) undec-5-ene (DBU).

* * * * *